US005700450A

United States Patent [19]
Gilchrest et al.

[11] Patent Number: 5,700,450
[45] Date of Patent: *Dec. 23, 1997

[54] METHODS FOR ENHANCING MELANIN SYNTHESIS IN MELANOCYTES USING DIACYGLYCEROLS AND USES THEREOF

[75] Inventors: Barbara A. Gilchrest, Brookline, Mass.; Philip R. Gordon, Philadelphia, Pa.

[73] Assignee: The Trustees of Boston University, Boston, Mass.

[*] Notice: The term of this patent shall not extend beyond the expiration date of Pat. No. 5,352,440.

[21] Appl. No.: 314,470

[22] Filed: Sep. 28, 1994

Related U.S. Application Data

[63] Continuation-in-part of Ser. No. 934,872, Aug. 21, 1992, Pat. No. 5,352,440, which is a continuation-in-part of Ser. No. 624,453, Dec. 10, 1990, abandoned, which is a continuation of Ser. No. 175,129, Mar. 30, 1988, abandoned, and a continuation of Ser. No. 625,236, Dec. 10, 1990, abandoned, and a continuation of Ser. No. 625,405, Dec. 11, 1990, abandoned.

[51] Int. Cl.$^6$ ............ A61K 7/42; A61K 31/22; A61K 31/225
[52] U.S. Cl. ............ 424/59; 514/546; 514/547; 514/548; 514/549
[58] Field of Search ............ 424/59; 514/546, 514/547, 548, 549

[56] References Cited

U.S. PATENT DOCUMENTS

| | | | |
|---|---|---|---|
| 4,443,546 | 4/1984 | Stemerman et al. | 435/240 |
| 4,508,706 | 4/1985 | Pawelek et al. | 424/60 |
| 4,618,484 | 10/1986 | Pawelek | 424/1.1 |
| 4,695,449 | 9/1987 | Pawelek | 424/1.1 |

FOREIGN PATENT DOCUMENTS

| | | |
|---|---|---|
| 0255964 | 2/1988 | European Pat. Off. |
| WO 91/07167 | 5/1991 | WIPO |
| WO 91/07168 | 5/1991 | WIPO |
| 94/04122 | 3/1994 | WIPO |

OTHER PUBLICATIONS

Sasakawa, N. et al., "Introduction of Ornithine Decarboxylase Activity by 1–Oleoyl–2–Acetyl–Glycerol in Isolated Mouse Epidermal Cells," *Biochemical & Biophys. Res. Comms.*, 128(2):913–920 (1985).

Smart, R.C. et al., "sn–1,2–Diacylglycerols Mimic the Effects of 12–O–tetradecanoylphorbol–13–acetate In Vivo by Inducing Biochemical Changes Associated with Tumor Promotion in Mouse Epidermis," *Carcinogenesis*, 7(11):1865–1870 (1986).

Wren, F. et al., "Ultraviolet–Mediated Melanogensis in Cultured Human Melanocytes is not Moderated by Prostaglandins E1, E2, or TPA," *Invest. Dermatol.*, 91(4):380 (Abstract 29) (1988).

Gordon, P.R. et al., "Human Melanogensis is Stimulated by Diacylglycerol," *Jour. of Invest. Derm.*, 93(5):700–702 (1989).

Korner, A. and Pawelek, J.P., "Activation of Melanoma Tyrosinase by a Cyclic AMP–Dependent Protein Kinase in a Cell–Free System," *Nature*, 267:444–447 (1977).

Nishizuka, Y., "Studies and Perspectives of Protein Kinase C," *Science*, 233:305–312 (1986).

Friedmann, P.S. and Gilchrest, B.A., "Ultraviolet Radiation Directly Induces Pigment Production by Cultured Human Melanocytes," *Journ. of Cell. Phys.*, 133:88–94 (1987).

Friedmann, P.S. et al., "Ultraviolet Stimulated Melanogenesis by Human Melanocytes is Augmented by Di–Acyl Glycerol but not TPA," *Journ of Cell. Phys.*,142:334–341 (1990).

Gordon, P.R. et al., "Relative Responsiveness of Cultured Human Epidermal Melanocytes and Melanoma Cells to Selected Mitogens," *Jour. of Invest. Derm.*, 87(6):723–727 (1986).

Ganong, B.R. and Bell, R.M., "Synthesis of Cell–Permeant Diacylglycerol Analogs for Structure–Function Analysis of Protein Kinase C and Other Enzymes," *Meth. of Enzym.*, 141:313–320 (1987).

Strålfors, P., "Insulin Stimulation of Glucose Uptake can be mediated by Diacylglycerol in Adipocytes," *Nature*, 335:554–556 (1988).

Bolognia, J.L., "Hairless Pigmented Guinea Pigs: A New Model for the Study of Mammalian Pigmentation," *Pigment Cell Res.*, 3:150–156 (1990).

Imokawa, G. et al., "Differential Analysis of Experimental Hypermelanosis Induced by UVB, PUVA, and Allergic Contact Dermatitis Using a Brownish Guinea Pig Model," *Arch. Dermatol. Res.*, 278:352–362 (1986).

Gilchrest, B.A. et al., "Selective Cultivation of Human Melanocytes from Newborn and Adult Epidermis," *Jour. of Invest. Dermat.*, 83:370–376 (1984).

Castagna, M., "Phorbol Esters as Signal Transducers and Tumor Promoters," *Biol. of the Cell*, 59:3–14 (1987).

Nordlund, J.J. et al., "Prostaglandin $E_2$ and $D_2$ but not MSH Stimulate the Proliferation of Pigment Cells in the Pinnal Epidermis of the DBA/2 Mouse," *Jour. of Invest. Dermat.*, 86(4):433–437 (1986).

Lerner, A.B. et al., "Transplantation of Human Melanocytes," *Jour. of Invest. Dermat.*, 89(3):219–224 (1987).

Halaban, R et al., "Tyrosinase Activity and Abundance in Cloudman Melanoma Cells," *Arch. of Biochem. and Biophys.*, 230(1):383–387 (1984).

Abdel, Z.A. et al., "Long–Term and Residual Melanotropin–Stimulated Tyrosinase Activity in S91 Melanoma Cells is Density Dependent," *In Vitro Cell. & Dev. Biol.*, 22(2):75–81 (1986).

(List continued on next page.)

*Primary Examiner*—Kevin E. Weddington
*Attorney, Agent, or Firm*—Hamilton, Brook, Smith and Reynolds, P.C.

[57] ABSTRACT

Methods for enhancing melanin synthesis in melanocytes, thereby increasing the melanin content of melanocytes with subsequent transfer of the melanic pigments to keratinocytes resulting in increased pigmentation of vertebrate skin and hair; melanocytes with increased melanin content produced by these methods; and uses thereof are disclosed.

17 Claims, 10 Drawing Sheets

OTHER PUBLICATIONS

Gordon, P.R. et al., "Regulation of Human Melanocyte Growth, Dendricity, and Melanization by Keratinocyte Derived Factors," *Jour. of Invest. Dermat.*, 92(4):565–572 (1989).

Gordon, P.R. et al., "Cultured Keratinocytes Release Factors that Increase Melanocyte Growth, Melanization and Dendricity," *J. Invest. Dermatol.*, 90:564 (Abstract) (1988).

Pittelkow, M.R. et al., "Serum–Free Culture of Normal Human Melanocytes: Growth Kinetics and Growth Factor Requirments," *J. of Cell. Phys.*, 140:565–576 (1989).

Gilchrest, B.A. et al., "A Culture System for the Study of Human Melanocytes Physiology," *Structure and Function of Melanin*, K. Jimbow (ed.) vol. 4 (Proceedings of the XIII Intl. Pigment Cell Conf.) Fuji–Shoin Co. Ltd., Sapporo, Japan pp. 1–13 (1987).

Nordlund, J.J. et al., "Mechanisms for Post–Inflammatory Hyperpigmentation and Hypopigmentation," *Advances in Pigment Cell Res.*, pp. 219–236 (1988).

Rosen, C.F. et al., "A Comparison of the Melanocyte Response to Narrow Band UVA and UVB Exposure In Vivo," *Journ. of Invest. Dermatol.*, 88(6):774–781 (1987).

Hadley, M.E. et al., "Biological Actions of Melanocyte–Stimulating Hormone," *Ciba Foundation Symposium*, 81 pp. 244–262 (1981).

Kitajima, Y. et al., "Biphasic Effects of 12–O–Tetradecanoylphorbol–13 Acetate on the Cell Morphology of Low Calcium–Grown Human Epidermal Carcinoma Cells: Involvement of Translocation and Down Regulation of Protein Kinase," *Cancer Res.*, 48:964–970 (1988).

Mori, T. et al., "Specificity of the Fatty Acyl Moieties of Diacyglycerol for the Activation of Calcium–Activated, Phospholipid–Dependent Protein Kinase", *J. Biochem.* 91:427–431 (1982).

Ganong, B.R. et al., "Specificity and Mechanism of Protein Kinase C Activation by sn–1,2–Diacylglycerols", *Proc. Natl. Acad. Sci. USA* 83:1184–1188 (1986).

Molleyresl L.P. and Rando, R.R., "Structural Studies on the Diglyceride–mediated Activation of Protein Kinase C", *J. Biol. Chem.* 263(29):14832–14838 (1988).

Bell, R.M., "Protein Kinase C Activation by Diacylglycerol Second Messengers," *Cell*, 45:631–632 (1986).

Smart, R.C. et al., "Comparison of the Effect of sn–1, 2–Didecanoylglycerol and 12–O–Tetradecanoylphorbol–13–acetate on Cutaneous Morphology, Inflammation and Tumor Promotion in CD–1 Mice," *Carcinogenesis*, 9(12):2221–2226 (1988).

Rando, R.R. and Kishi, Y., "Structural Basis of Protein Kinase C Activation by Diacylglycerols and Tumor Promoters," *Biochemistry*, 31:(8):2211–2218 (1992).

Agrin, P.P., et al., "Diacylglycerol–Induced melanogenesis in Skh–2 Pigmented Hairless Mice," *Photoderm. Photoimmuno. & Photomedicine*, 8(2):51–56 (1991).

Brooks, G., et al., "Growth of Melanocytic Cells is Associtated with Down–Regulation of Protein Kinase C $\alpha$, $\delta$, and $\epsilon$ Isoforms," *J. Biol. Chem.*, 268(32):23868–23875 (1993).

METHODS FOR ENHANCING MELANIN SYNTHESIS IN MELANOCYTES USING DIACYGLYCEROLS AND USES THEREOF

RELATED APPLICATIONS

This application is a continuation-in-part of Ser. No. 07,934,872 filed Aug. 21, 1992, now U.S. Pat. No. 5,352,440 which is a continuation-in-part of Ser. No. 07/624,453 filed Dec. 10, 1990, now abandoned, which is a continuation of Ser. No. 07/175,129, filed Mar. 30, 1988, now abandoned, and of Ser. No. 07/625,236, filed Dec. 10, 1990, now abandoned and Ser. No. 07/625,405, filed Dec. 11, 1990, now abandoned. The teachings of these applications are incorporated herein in their entirety by reference.

GOVERNMENT SUPPORT

The invention described herein was supported in whole, or in part, by grants from the United States Department of Agriculture (Contract No. 533K-06-5-10) and the National Institutes of Health (Grant No. CA 45687). The United States government has certain rights in this invention.

BACKGROUND OF THE INVENTION

Melanins are a class of structurally related compounds that serve as the principal pigment (color) of vertebrate skin, hair, fur and feathers. Melanin pigmentation is largely responsible for normal skin and hair color, and provides protection against ultraviolet light damage from sunlight and other light sources. Melanins are synthesized exclusively by specialized cells termed "melanocytes" found in the skin and hair follicles. Once synthesized, melanin is concentrated in the form of small pigmented particles, named melanosomes, which are then transferred via the cellular dendrites (extensions) of the melanocytes to the surrounding keratinocytes, the most abundant cell type in the epidermis and the hair bulb. The rate of melanin synthesis, and the subsequent transfer of melanin by melanocytes via their dendrites, appear to be influenced by ultraviolet light exposure.

Darker skin pigmentation is considered desirable by many persons, socially and aesthetically. At present, the most common means of darkening skin is sun-tanning, using either natural sunlight or specially designed ultraviolet light sources (tanning lamps).

However, extended exposure of human skin to ultraviolet light is well known to have adverse long and short term health consequences, specifically skin cancer and photoaging (long term) and the risk of painful sunburn and keratitis (short term). Furthermore, light-skinned individuals are highly susceptible to sun-induced skin cancers, face a higher risk of melanoma (skin cancer), and incur photoaging or dermatoheliosis, a condition characterized by wrinkling, irregular pigmentation, and surface roughness. However, even darker skinned individuals exposed to prolonged sunlight incur a high risk of skin cancer and exacerbated aging.

Some individuals are unable to achieve even normal pigmentation due to abnormal conditions such as vitiligo, piebaldism, albinism, and other hypopigmentation disorders, or as the result of certain inflammatory processes. The result of such abnormal conditions, in the extreme, is total depigmentation of both hair and skin. In less severe instances, some hypopigmentation disorders result in patchy white areas within the skin and hair. All of these conditions can cause severe cosmetic and psychological problems.

Melanocytes and melanin content are also responsible for the pigmentation of hair, fur and feathers. For example, graying of hair is due to a decrease in number or activity of the melanocytes residing in the hair bulb. In nonhuman instances, changes in melanocyte content and melanin synthesis rate result in changes in the color of pelage, fur, wool, and other kinds of animal hair.

The ability to increase melanin synthesis, and thus increase the melanin content of melanocytes and the number of melanosomes transferred to the surrounding epidermal and hair-bulb keratinocytes, would provide an alternate method of darkening skin pigmentation without the hazards of ultraviolet irradiation. Moreover, increasing the melanin content of hair would provide a method for darkening graying hair. Furthermore, the ability to maintain melanin production would minimize discoloration in fur, wool, feathers, and other animal hair counterparts and would permit production of biologically engineered fur, wool, and feathers with desired levels of pigmentation.

SUMMARY OF THE INVENTION

The present invention relates to methods for enhancing melanin synthesis in vertebrate melanocytes, thereby increasing the melanin content of melanocytes and, thus, increasing pigmentation of the skin and hair in vertebrates, such as in humans. As described herein, in the methods of the present invention, a diacylglycerol which enhances melanin synthesis in melanocytes is contacted with melanocytes, or delivered to the melanocytes, thereby enhancing or inducing melanin synthesis in the melanocytes and increasing the melanin content of the melanocytes. Once synthesized, the melanin is concentrated in the melanosomes. The increased melanin content in melanocytes results in increased pigmentation, or darkened color, of the skin and hair because of the subsequent transfer of the melanosomes to the surrounding keratinocytes in the epidermis and hair follicles. The melanocytes that are contacted with the diacylglycerol may be present in vertebrate skin, hair, fur, or feathers.

The term diacylglycerol, or DAG, as used herein, includes the naturally-occurring 1,2-diacylglycerol, and synthetic DAG analogues and derivatives. The DAGs used in the invention will be defined more precisely in the detailed description of the invention. DAGs are able to induce melanin synthesis and thus, produce an increase in melanin content in melanocytes without altering melanocyte proliferation. DAGs are therefore selective in their biological action and cellular function and are generally able to induce melanin synthesis specifically within pre-existing melanocytes. Particularly useful in the present method is a water dispersible analogue of DAG, 1-oleoyl-2-acetyl-glycerol, or OAG, 1,2-dioctanoylglycerol and 1,2-didecanoylglycerol.

DAGs can be used to treat a variety of conditions resulting from decreased production of, or complete absence of, melanin in melanocytes. Such conditions include vitiligo, tinea versicolor, albinism and other hypopigmentation conditions. DAGs can also be used cosmetically to tan the skin, to prevent or delay hair-graying and darken hair color, as well as prevent discoloration of animal fur, wool, feathers and other animal hair counterparts.

In a preferred embodiment, a DAG which enhances melanin synthesis, or a combination of such DAGs, can be combined in admixture with a biologically compatible fluid carrier to form a topical formulation which can be applied to, or contacted with, skin areas or hair-covered areas to be pigmented. The DAGs increase the melanin content of the skin or hair-covered areas in vivo thus pigmenting skin or hair. This embodiment is particularly useful as a method for pigmenting skin and hair of a human being.

In another embodiment, the present invention provides a method for in vitro culture of melanocytes in a conventional culture medium for melanocytes, comprising adding to culture medium an effective amount of a diacylglycerol which enhances melanin synthesis in the melanocytes, thereby producing melanocytes with increased melanin content (also referred to herein as "activated" melanocytes). The present invention also encompasses the activated melanocytes with increased melanin content produced by a method of culture comprising contacting the melanocytes in a conventional culture medium with an effective amount of a diacylglycerol which enhances melanin synthesis in melanocytes.

The present invention also provides a method for the treatment of hypopigmented conditions in vertebrates, for example, acquired or congenital white patches of skin. The methods of treating such hypopigmented conditions comprises the implantation of skin grafts on areas of hypopigmented skin (e.g., vitiligo patches). These skin grafts can comprise melanocytes activated by having been cultured in a culture medium containing an effective amount of a diacylglycerol for stimulating melanin synthesis within the melanocytes.

DETAILED DESCRIPTION

Figure 1A:
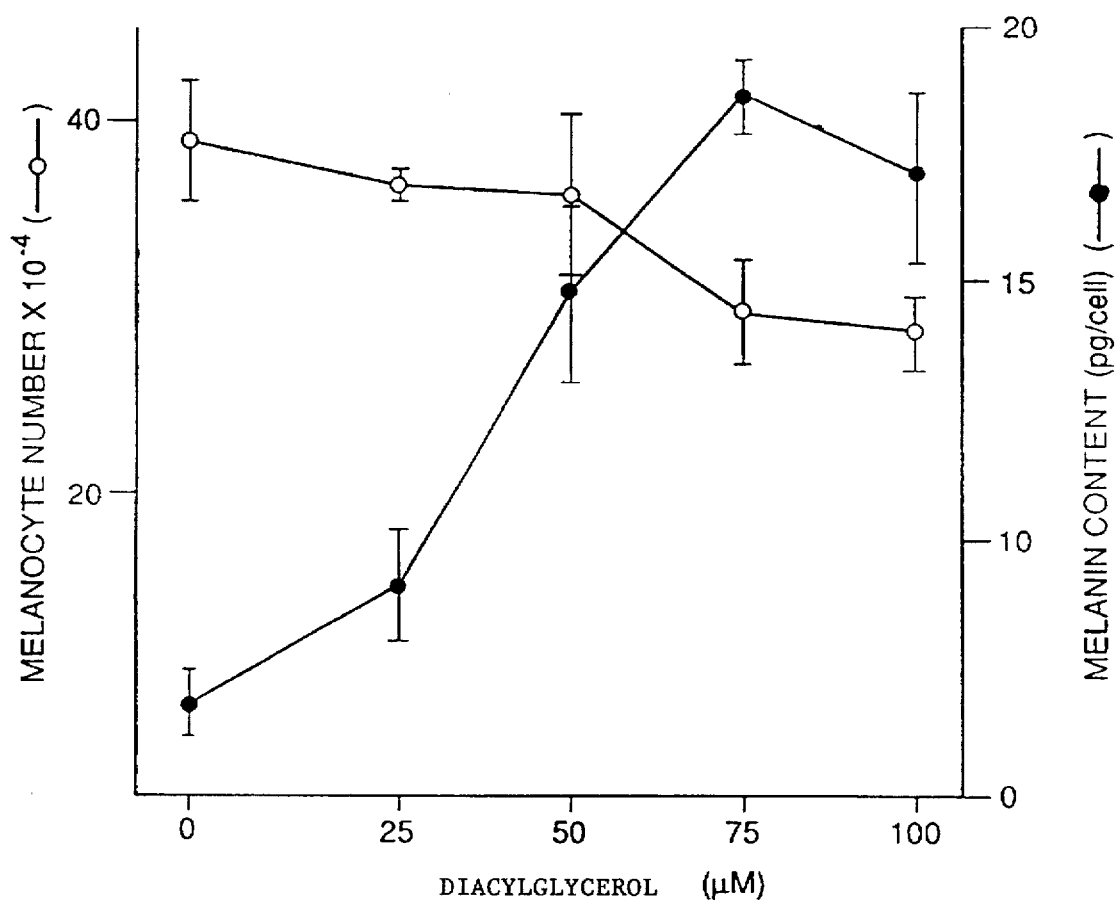
FIG. 1a and 1b are graphs illustrating the effects of a diacylglycerol, 1-oleoyl-2-acetyl-glycerol, upon human melanocyte proliferation and melanin content.

The present invention relates to methods of inducing melanin synthesis in melanocytes, thereby increasing the melanin content of melanocytes and, thus, increasing pigmentation after the subsequent transfer of the melanic pigments to the surrounding keratinocytes. The term pigmentation as used herein, means the deposit of melanin in the form of melanic pigments, or melanosomes, in the skin, hair, fur and feathers of vertebrates, including humans, in a sufficient amount to produce a visual pigmentation effect. The deposit of melanin can manifest itself visually as a brown or dark brown coloring of skin and hair.

Cell membranes are composed primarily of diverse lipid species that can interact with membrane-associated proteins, some of which require specific lipid: protein interactions with the membrane for activation.

One such lipid-requiring protein is protein kinase C (PKC), a regulatory enzyme involved in signal transduction. PKC represents a family of serine-threonine kinases, present in all cell types, which mediate a diverse array of stimulus-response pathways, including release of serotonin from platelets, release of transmitters from neurons and cell proliferation in response to growth factors such as Platelet Derived Growth Factor (PDGF).

PKC, located in the cytoplasm in its inactive form, translocates to the membrane on activation, a transition that requires membrane phospholipid, phosphatidylserine and calcium, in addition to a second lipid species, diacylglycerol (DAG). In fact, specific DAGs released from the membrane are the only known physiologic regulators of PKC. (Rando, R. R. and Kishi, Y., "Structural Basis of Protein Kinase C. Activation by diacylglycerols and Tumor Promoters" *Biochem.* 31:2211–2218, (1992)).

Normally, very little free DAG is found in membranes, but in response to extracellular stimuli, DAGs are cleaved from inositol phospholipids by the action of phospholipase C (Bell, R. M., "Protein Kinase C Activation by Diacylglycerol Second Messengers" *Cell* 45:631–632 (1986)). Once released, certain DAGs are able to bind to the regulatory domain of PKC and cause activation. Previous work as determined, that in addition to strict stereospecificity, DAGs capable of activating PKC must have oxygen ester carbonyl groups attached to carbon atoms $C_1$ and $C_2$ of the glycerol backbone, and a hydroxyl group on $C_3$ (Ganong, B. R., et al., "Specificity and Mechanism of Protein Kinase C Activation by sn-1,2-diacylglycerols" *Proc. Natl. Acad. Sci.*, 83:1184–1188 (1986)). Finally, the fatty acyl side chains attached to $C_1$ and $C_2$ must be of sufficient length, preferably with one unsaturated chain to allow for enzyme activation (Mori, T. et al., "Specificity of the Fatty Acyl Moieties of Diacylglycerol for the Activation of Calcium-Activated Phospholipid-Dependent Protein Kinase" *J. Biochem.*, 91:427–431 (1982)). This unsaturated fatty acyl moiety is postulated to intercalate with membrane phospholipids to allow the specific protein: lipid interaction to occur (Mori, T. et al., "Specificity of the Fatty Acyl Moieties of Diacylglycerol for the Activation of Calcium-Activated Phospholipid-Dependent Protein Kinase" *J. Biochem.*, 91:427–431 (1982)).

Chemical Structure And Occurrence of Diacylglycerol

As used herein, the term (DAG) includes naturally-occurring diacylglycerols, as well as synthetic analogues and derivatives of naturally-occurring diacylglycerols.

Synthetic DAG analogues have been prepared that also have biological activity as activators of PKC. (Ganong, B. R. and Bell, R. M., *Meth. Enzymol.* 141:313–320 (1987)).

DAG analogues can be prepared by conventional methods and have general chemical structures of Compounds A, B, and C, as follows:

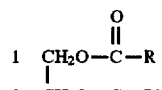

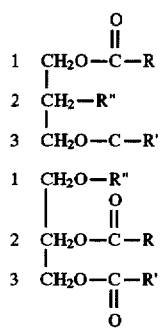

in which R and R' represent independently a hydrogen atom or a carbon containing moiety which in the present invention has preferably from 1 to 23 carbon atoms. Accordingly, the radical

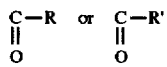

will preferably contain from 1 to 24 carbon atoms.

In the present invention, at least one of R and R' is a long-chain radical of a carboxylic acid and may contain 1 or more carbon-carbon double bonds. This long chain carboxylic acid usually has from 14 to 24 carbon atoms. In most instances, R and R' are chemically different in the composition. (Ganong, B. R. and Bell, R. M., Meth. Enzymol. 141:313–320 (1987)).

In comparison, R" can be any chemical entity which does not form a carbon ester linkage with the adjoining carbon atom in the glycerol structure. Accordingly, R" may include a hydroxyl group, a phosphate group, a sulfur atom, an ether group, a halide, a nitrogen containing entity, or a hydrogen. (Ganong, B. R. and Bell, R. M., Meth. Enzymol. 141:313–320 (1987)).

Diacylglycerols Useful in the Present Method

Diacylglycerols (DAGs) useful in the present method are those DAGs, naturally-occurring, as well as synthetic analogues, which are biologically active (i.e., induce melanin synthesis) and thus, increase melanin content in melanocytes under in vivo and/or in-vitro conditions. The naturally occurring DAGs are derivatives of phosphatidylinositol and usually contain a long-chain mono-unsaturated fatty acid acylated to the number one carbon position in the glycerol structure. Also, DAGs typically contain a polyunsaturated fatty acid, primarily arachidonic acid, acylated to the number two carbon position in the glycerol structure. More specifically, the DAGs of the present invention comprise a hydroxyl in the three position and one or two carboylic acid esters having from one to twenty-four carbon atoms.

A preferred DAG in the present method is 1-oleoyl-2-acetyl-glycerol, or OAG, a synthetic DAG analogue. OAG is particularly useful because of its solubility in water and its ability to produce a dose-dependent response in melanin content with no concomitant effect upon proliferation and/or growth of melanocytes. Additionally, other preferred DAGs contain a free hydroxyl group at the number three carbon position in the glycerol structure and have a three carbon backbone structure similar to glycerol. Other preferred DAGs are 1,2-dioctanoylglycerol and 1,2-didecanoylglycerol.

The present invention has evidenced that DAGs are biologically active and potent for stimulation of melanin synthesis within melanocytes. These DAGs include but are not limited to:

Diacylglycerol Analogues 1,2-diformylglycerol
1,2-diacetylglycerol
1,2-dibutanoylglycerol
1,2-dihexanoylglycerol
1,2-dioctanoylglycerol
1,2-didecanoylglycerol
1,2-didodecanoylglycerol
1,2-diteradecanoylglycerol
1,2-dihexadecoylglycerol
1,2-dioctadecanoylglycerol
1,2-dieicosanoylglycerol
1,2-didocosanoylglycerol
1,2-ditetracosanoylglycerol
1,2-dioleoylglycerol
1,2-dilinoleoylglycerol
1,2-dilinolenoylglycerol
1,2-arachidonoylglycerol
1-octanoyl-2-formyl-glycerol
1-octanoyl-2-acetyl-glycerol
1-octanoyl-2-butanoyl-glycerol
1-octanoyl-2-hexanoyl-glycerol
1-octanoyl-2-decanoyl-glycerol
1-octanoyl-2-dodecanoyl-glycerol
1-octanoyl-2-tetradecanoyl-glycerol
1-octanoyl-2-hexadecanoyl-glycerol
1-octanoyl-2-octadecanoyl-glycerol
1-octanoyl-2-eicosanoyl-glycerol
1-octanoyl-2-docosanoyl-glycerol
1-octanoyl-2-tetracosanoyl-glycerol
1-octanoyl-2-palmitoyl-glycerol
1-octanoyl-2-oleoyl-glycerol
1-palmitoyl-2-formyl-glycerol
1-palmitoyl-2-acetyl-glycerol
1-palmitoyl-2-butanoyl-glycerol
1-palmitoyl-2-hexanoyl-glycerol
1-palmitoyl-2-octanoyl-glycerol
1-palmitoyl-2-decanoyl-glycerol
1-palmitoyl-2-dodecanoyl-glycerol
1-palmitoyl-2-tetradecanoyl-glycerol
1-palmitoyl-2-hexadecanoyl-glycerol
1-palmitoyl-2-octadecanoyl-glycerol
1-palmitoyl-2-eicosanoyl-glycerol
1-palmitoyl-2-docosanoyl-glycerol
1-palmitoyl-2-oleoyl-glycerol
1-palmitoyl-2-linoleoyl-glycerol
1-palmitoyl-2-arachidonoyl-glycerol
1-oleoyl-2-formyl-glycerol
1-oleoyl-2-acetyl-glycerol
1-oleoyl-2-butanoyl-glycerol
1-oleoyl-2-hexanoyl-glycerol
1-oleoyl-2-octanoyl-glycerol
1-oleoyl-2-decanoyl-glycerol
1-oleoyl-2-dodecanoyl-glycerol
1-oleoyl-2-tetradecanoyl-glycerol 1-oleoyl-2-palmitoyl-glycerol
1-oleoyl-2-linoleoyl-glycerol
1-oleoyl-2-arachidonoyl-glycerol
1-hexanoyl-2-formyl-glycerol
1-hexanoyl-2-acetyl-glycerol
1-hexanoyl-2-butanoyl-glycerol
1-hexanoyl-2-octanoyl-glycerol
1-hexanoyl-2-decanoyl-glycerol
1-hexanoyl-2-dodecanoyl-glycerol
1-hexanoyl-2-tetradecanoyl-glycerol
1-hexanoyl-2-hexadecanoyl-glycerol
1-hexanoyl-2-octandecanoyl-glycerol
1-hexanoyl-2-eicosanoyl-glycerol
1-hexanoyl-2-palmitoyl-glycerol
1-hexanoyl-2-oleoyl-glycerol
1-hexanoyl-2-linoleoyl-glycerol
1-hexanoyl-2-arachidonoyl-glycerol Effects Of Diacylglycerols on Human Melanocytes The following experiments investigate the biological effects of DAG upon human melanocytes and reveals the effects of pretreatment of human melanocytes with specific agents prior to incubation with a DAG.

Figure 1B:
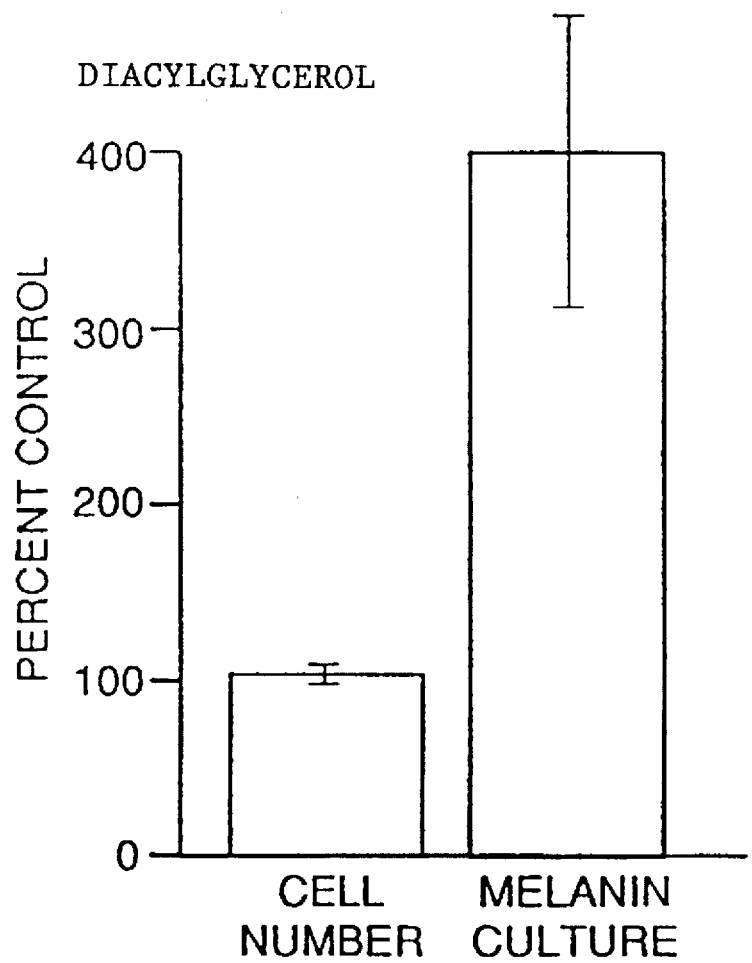

A first set of experiments was performed which used human melanocytes cultured as described in Example 1. Human melanocytes were combined with 1-oleoyl-2-acetyl-glycerol (OAG) in complete melanocyte medium and incubated together for a period of 6 days at 37° C. Melanin content of the cells was determined as described in Example 2. The results are graphically illustrated by FIGS. 1a and 1b, which show a dose dependent response of increased melanin content at concentration levels ranging from 25-100 µM OAG, with no significant effect on melanocyte proliferation or growth.

At a concentration of 100 µM, OAG produced an average of a 4-fold increase in melanocyte melanin content per cell over the untreated control (i.e., melanocytes cultured as in Example 1, combined with complete melanocyte medium and incubated as were treated cells). Importantly, OAG did not significantly affect human melanocyte growth.

A second set of experiments was conducted in which the cultured human melanocytes were first pretreated with tetradecanoyl phorbol-13-acetate (TPA), a known activator of protein kinase C. It is known that TPA first stimulates and subsequently, profoundly suppresses PKC activity for a prolonged period.

Initially, the human melanocytes were obtained and grown as previously described in Example 1. Subsequently, the cultured human melanocytes were combined with 100 nM of TPA in melanocyte medium and incubated at 37° C. for 24 hours. OAG was then added and the culture incubated again for 6 days. The melanin content of the cells was then evaluated according to Example 2. The results are graphically illustrated by FIGS. 2 and 3 respectively.

Figure 2:
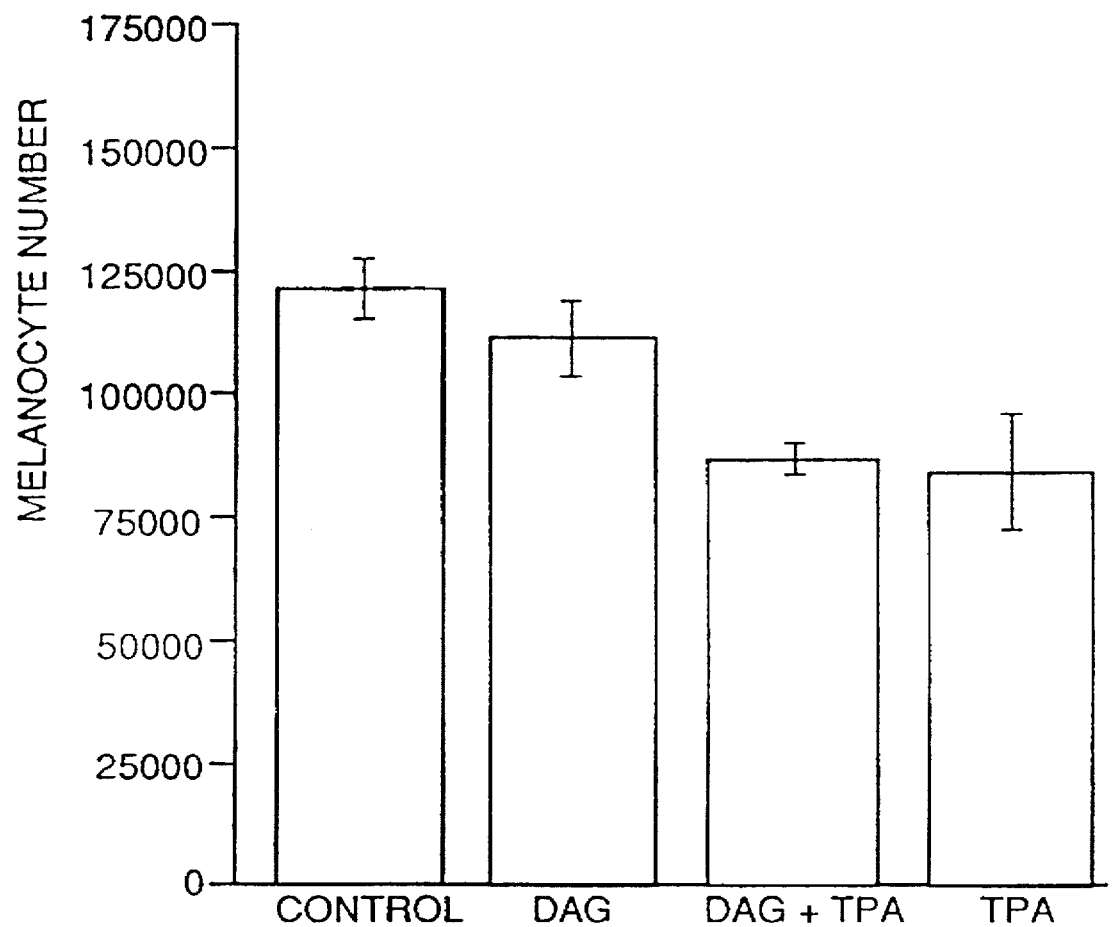
FIG. 2 is a graph illustrating the effects of a diacylglycerol, 1-oleoyl-2-acetyl-glycerol, upon the proliferation of human melanocytes when administered alone and after pretreatment with a phorbol ester.
Figure 3:
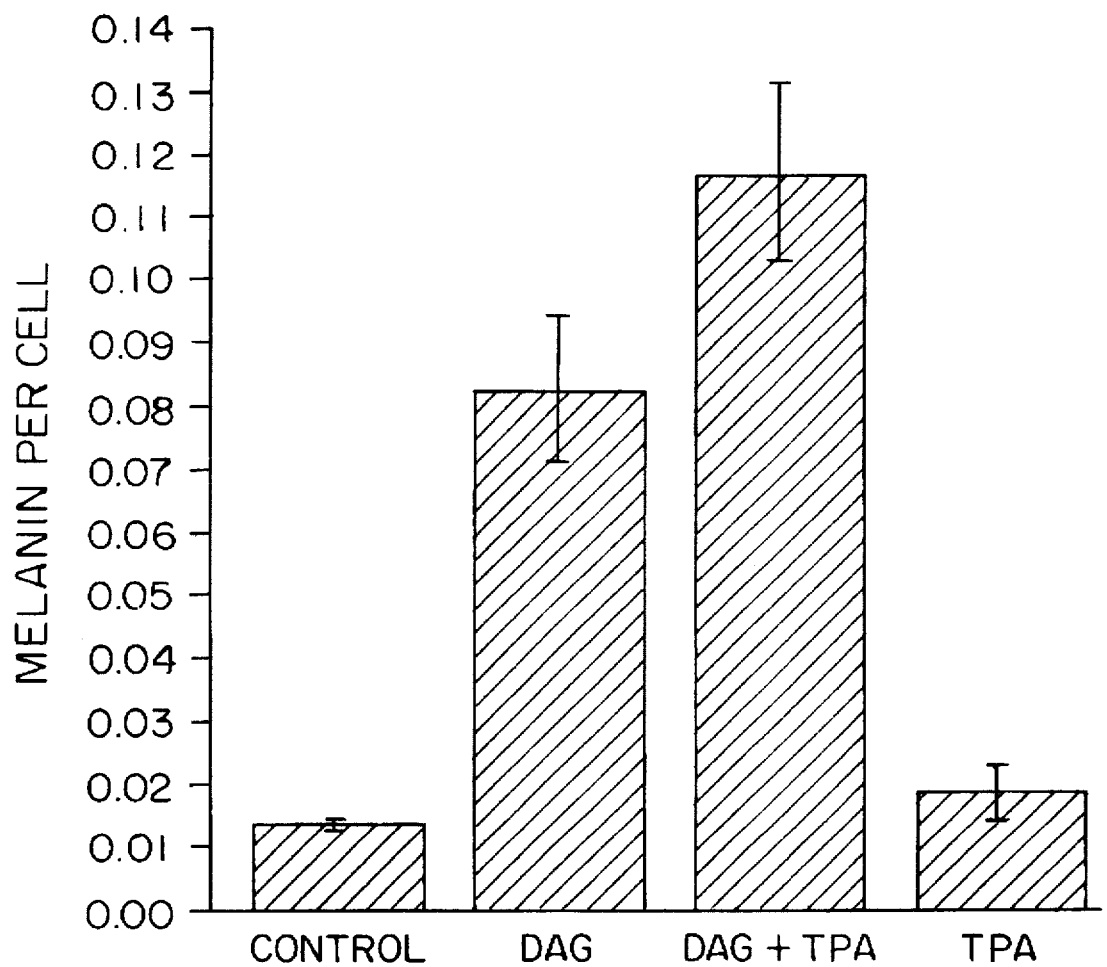
FIG. 3 is a graph illustrating the effects of a diacylglycerol, 1-oleoyl-2-acetyl-glycerol, upon melanin production in human melanocytes when administered alone and after pretreatment with a phorbol ester.

FIG. 2 demonstrates that neither OAG, nor the pretreatment with TPA, or their combination, has any substantial affect on human melanocyte proliferation. However, in comparison, FIG. 3 demonstrates significant increases in melanin content per human melanocyte as a function of TPA pretreatment in combination with OAG treatment. Thus, pre-exposure to TPA actually enhanced the OAG effect on melanin synthesis. Consequently, for maximum melanin production, it may be desirable to pretreat human melanocytes prior to contact with the chosen DAG.

Effects Of Diacylglycerols On Non-Human Melanocytes

This set of experiments was performed to evaluate the effect of DAG on melanocytes derived from non-human sources, rather than humans. In these experiments, murine S91 melanoma cells were grown and maintained in culture using conventional techniques (Friedmann, P. S. and Gilchrest, B. A., *J. Cell. Physiol.* 133:88–94 (1987)). The S91 melanoma cells were then combined with 100 µM of OAG, or with 100 µM of 3-isobutyl-1-methylxanthine (IBMX), which increases cAMP levels and also induces melanin synthesis in S91 melanoma cells. Each chemical agent was combined with the S91 melanoma cells in Dulbecco's Minimal Eagle's Medium containing 2% FBS and incubated at 37° C. for 7 days. The results are graphically illustrated by FIGS. 4 and 5, respectively.

Figure 4:
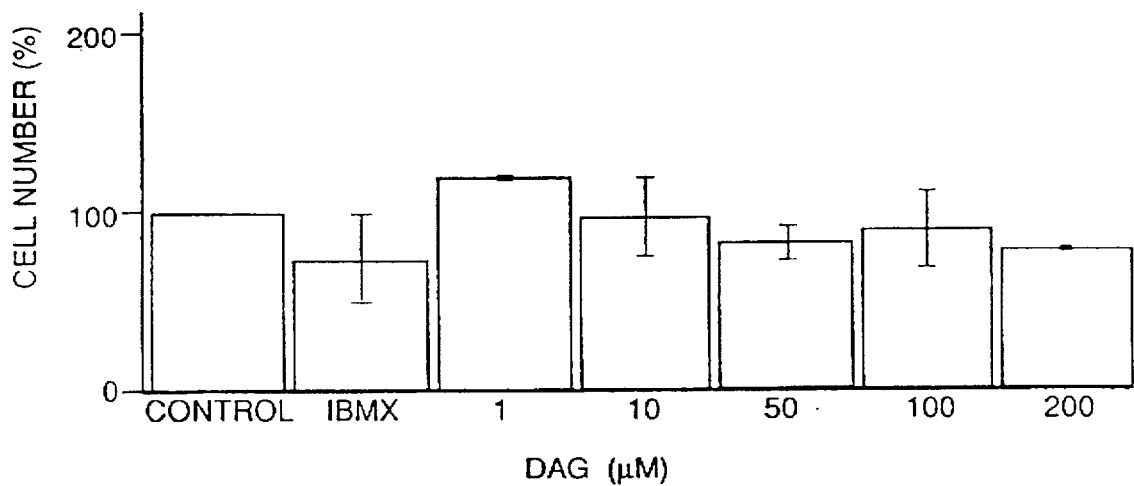
FIG. 4 is a graph illustrating the effects of a diacylglycerol, 1-oleoyl-2-acetyl-glycerol, on the proliferation of S91 murine melanoma cells in culture.

FIG. 4 demonstrates that OAG at concentrations ranging from 1–200 µM failed to induce proliferation of S91 melanoma cells. IBMX was similar in effect and also failed to produce any cellular growth. In comparison, FIG. 5 reveals major differences between the ability of OAG and IBMX to induce an increase in melanin production. Clearly, IBMX at a concentration of 100 µM caused a major increase in melanin production in S91 melanoma cells. In comparison, OAG under the experimental conditions indicated, failed to induce any substantial increase in melanin production in comparison to controls.

These results suggest that the biological effects of DAG are selective and discriminatory in accordance with the source of origin of the melanocytes. Specifically, under the conditions used, OAG has no meaningful effect on transformed S91 murine melanoma cells. On the other hand, contact of OAG to human melanocytes results in substantial increases in melanin content without concomitant cell proliferation of the human melanocytes. As described in Example 3, 1,2-dioctanoylglycerol was also effective to increase melanin synthesis in cultured human melanocytes.

In Vivo Effects of Diacylglycerols

Experiments were also conducted in adult guinea pigs to evaluate the effects of DAGs in vivo. Guinea pigs are accepted models for studies of the human pigmentary system because they contain melanin in the epidermis, as well as in hair follicles, which is similar to the distribution of melanin in human skin. (Bolognia, J. L., et al., *Pigment Cell Res.* 3:150 (1990); Imokawa, G., *Arch. Dermatol. Res.* 278:352 (1986)).

To determine whether OAG (M.W. 398) can increase melanin production in vivo, four separate doses of increasing concentrations of OAG (20–60 mg/ml) in propylene glycol were applied daily for five days to four shaved guinea pigs, as described in detail in Example 4. Dose-dependent increased pigmentation (+1 to +3 on a 0–4 scale) was visible after 17 days in 3 of 4 animals. Epidermal melanin content was greater than twice that of untreated or vehicle-treated sites, as assessed by computerized image analysis of Fontana-Masson stained biopsy cross-sections. This increased pigmentation persisted for 10–14 weeks. In a second study using the range of OAG concentration 10–60 mg/ml (25–450 mM), a similar rise in epidermal melanin content was seen in those test sites that received higher OAG concentrations. In a third experiment, guinea pigs received twice daily separate applications of OAG, dipalmitoylglycerol ($diC_{16}$, M.W. 568), dioctanoylglycerol ($diC_8$, M.W. 344) 50 mg/ml (i.e., 5% by weight, 145 mM), 20µ/application, and propylene glycol vehicle alone for 5 days. Increased pigmentation (+1 to +2) was visible after 10 days in the OAG and $diC_8$ sites but not in $diC_{16}$ or vehicle sites. These results correlate with the reported ability to these compounds to activate protein kinase C (PKC) for which DAG is the known physiologic effector. In a final experiment, guinea pigs received OAG 25 mg/ml, 3 times daily to one test site, and once daily UVB (70 m/cm$^2$)

radiation to another. The OAG and UVB test sites developed comparable even +2 to +3 pigmentation. Our data demonstrate that topically applied DAGs can produce a long-lasting increase in epidermal pigmentation, presumably through PKC activation, which is clinically and histologically indistinguishable from UV-induced tanning.

Figure 6:
FIG. 6 is a photograph showing increased pigmentation of both skin and hair in guinea pigs treated with a diacylglycerol, 1-oleoyl-2-acetyl-glycerol.

Additional data was obtained to demonstrate that topical application of a diacylglycerol (OAG) increases pigmentation of both skin and hair in treated guinea pigs, and that this effect is long-lasting. Guinea pigs were treated as described in Example 4, with 60 mg/ml of OAG, twice daily for five days. After three months, the guinea pigs were examined. As shown in FIG. 6, the area of interest is the upper left-hand corner. Within the shaved area, a hyperpigmented semi-circle is visible. This represents increased epidermal pigmentation. The extension of this semi-circle into unshaved area (to the edge of the photograph) is an area of hyperpigmented hair.

These experiments clearly demonstrate the ability of diacylglycerols to increase epidermal pigmentation in-vivo in a manner clinically and histologically identical to normal sun-induced tanning. Importantly, this pigmentation occurs irrespective of exposure to a source of irradiation, such as ultraviolet irradiation or sunlight irradiation. In addition, under the conditions described herein, it is demonstrated that diacylglycerols increase pigmentation of hair. Thus, these data establish the ability of a DAG to induce melanogenesis in melanocytes, in-vivo.

Diacylglycerol Administration And Manner Of Use

DAGs may be employed in the methods of the present invention as follows: in a method for pigmenting (coloring) skin grafts, allografts, and autografts in-vitro and in-vivo; for treating hypopigmentation disorders such as vitiligo, albinism, piebaldism, and post-inflammatory hypopigmentation; as a sun-light independent human skin tanning agent; as a tanning accelerator in the presence of natural sunlight; as a treatment for darkening, or repigmenting, hair in-vivo; for preventing gray (depigmented) hair in-vivo; and for pigmenting darkly colored animal pelage, fur, and wool in-vivo.

DAGs are particularly useful to induce melanin synthesis in humans to tan the skin in the absence of sunlight; to accelerate skin tanning in the presence of natural sunlight; and to provide a treatment to darken gray (depigmented) hair or to prevent or delay hair graying.

It is intended that the DAGs of the present method be employed both in-vivo and in-vitro. For in-vivo use, it is desirable that delivery of a DAG to melanocytes be accomplished by topical administration of an effective amount of one or more DAGs directly to the skin or hair of vertebrates. As defined herein, an effective amount of a DAG is that amount of DAG capable of enhancing melanin synthesis in melanocytes. An effective amount of DAG capable of increasing melanin synthesis in vitro can be determined as described in Examples 1, 2 and 3 using cell culture techniques well known to those of skill in the art. An effective amount of a DAG capable of increasing melanin synthesis in melanocytes in vivo can be determined as described in Example 4. An effective amount of DAG resulting in pigmentation of skin and hair can be determined by visual inspection.

The DAGs of the present invention are intended to be admixed in a physiologically acceptable carrier suitable for topical application such as a gel, an ointment, a lotion, or a cream and will include such carriers as water, glycerol, alcohol, propylene glycol, fatty alcohols, triglycerides, fatty acid esters, or mineral oils.

Other possible topical carriers are liquid petrolatum, isopropyl palmitate, polyethylene glycol, ethanol (95%), polyoxyethylene monolauriate (5%) in water, sodium lauryl sulfate (5%) in water. Other materials such as anti-oxidants, humectants, viscosity stabilizers, and similar agents may be added as necessary. Formulations of DAG compositions suitable for use in the present invention are described in detail in Examples 5–9.

In addition, in certain instances, it is expected that the DAGs described herein may be disposed within devices placed upon, in, or under the skin; such devices include patches, implants, and injections which release the DAG into the skin either by passive or active release mechanisms.

In a preferred embodiment, for in vivo use, the diacylglycerol is present in a composition containing from 0.1 to 10%, and preferably from 1 to 5% by weight of diacylglycerol with respect to the total weight of the composition. However, the actual preferred amounts of DAG to be administered will vary according to the specific compound being utilized, the particular compositions formulated, the mode of application, and the particular site of the individual being treated. The concentration of DAG effective to increase melanin synthesis and thus, increase melanin content of melanocytes can be determined using known, conventional pharmacological protocols and evaluated using the cell culture and animal model described herein.

Alternatively, for in-vitro use with cultures of vertebrate melanocytes, the DAG may be added directly to the culture media surrounding the living cells at a concentration sufficient to induce melanin synthesis, and thus increase melanin content in the cultured melanocytes. Determinations of inhibitory and toxic concentrations for the DAG can also be made using known methods and evaluated using techniques described herein, and other methods known to those skilled in the art. In a preferred embodiment, the diacylglycerol is present in the culture medium in a concentration range from 10 µM to 1000 µM, and even more preferably from 50 µM to 300 µM.

For example, melanocytes can be treated in vitro to enhance melanin synthesis and increase their melanin content. Melanocytes can be obtained from vertebrate sources, preferably humans, and cultured under conditions sufficient for their proliferation. These cultured, melanocytes are then contacted with an effective amount of a diacylglycerol. The diacylglycerol can be added directly to the culture medium, for example, a described in Example 3. The contact with DAG can be a single contact, or multiple contacts on subsequent days of culture. After sufficient time to permit the melanin content of the cultured cells to increase, the cells are harvested. Such treated melanocytes are referred to herein as activated melanocytes. Activated melanocytes can be used to treat vertebrates, especially humans, suffering from hypopigmentation conditions (e.g., vitiligo), for example, by providing skin grafts comprising activated melanocytes to be grafted on to areas of the vertebrate to be treated.

The invention is further illustrated by the following examples, which are not intended to be limiting in any way.

EXAMPLE 1

Melanocyte Cell Culture

Neonatal foreskins obtained within two hours of elective circumcision were the source of human keratinocytes and melanocytes. The epidermis was separated from the dermis after overnight incubation in 0.25% trypsin. Melanocytes were established in primary culture from epidermis prepared according to the procedure of Gilchrest et al. (*J. Invest. Dermatol.* 83:370–376 (1984)).

In brief, operative specimens were cut into fragments, rinsed in calcium-free phosphate-buffered saline (PBS); and incubated in 0.25% trypsin (GIBCO) overnight at 4° C. The epidermal portions of the fragments were separated from the dermis with forceps; incubated for 10 minutes in 0.02% EDTA at 37° C.; vortexed to yield a single cell suspension; inoculated at a concentration of $10^6$ cells per 35-mm dish in melanocyte growth medium; and maintained at 37° C. in 8% carbon dioxide and 92% air. Cultures were provided with fresh melanocyte growth medium three times weekly. Melanocyte growth medium is a serum-free medium, Medium 199 (GIBCO 400–1100), supplemented with 10 ng/ml epidermal growth factor, 10 nM triodothyrine, 10 µg/ml transferrin, 10 µg/ml insulin, 1 nM cholera toxin and 100 µg/ml bovine hypothalamic extract.

EXAMPLE 2

Melanocyte Bioassay

Melanocytes were seeded at $2\times10^4$ cells per 35 mm dish and combined with DMEM supplemented with 10 µg/ml insulin, $10^{-9}$M triiodothyrine, 10 µg/ml transferrin, $1.4\times10^{-6}$M hydrocortisone, 10 ng/ml epidermal growth factor, $10^{-9}$M choleragen, 2% FBS and 100 µg/ml of BHE, now designated as complete melanocyte medium. After 24 hours incubation at 37° C., the melanocyte cultures, in duplicate or triplicate, received one of the following: free complete melanocyte medium or DAG. Each melanocyte culture was then incubated for 6–7 days at 37° C.

Subsequently, each melanocyte culture was harvested, washed with 0.4 mM EDTA in PBS, treated with 1 ml of a mixture containing 0.13% trypsin and 0.2 mM EDTA, then incubated approximately 10 minutes at 37° C. followed by addition of 1 ml of PBS. A 0.5 ml aliquot of each resulting suspension was diluted to 10 ml total volume using isotonic saline and processed using a particle counter (Model ZM, Colter Science).

To determine melanin content, the remaining suspension was centrifuged for 5 minutes in a microcentrifuge. The supernatant was discarded and the resulting cell pellet dissolved in 0.1 ml of a 1M NaOH which was subsequently diluted with 0.4 ml of water. Melanin concentration was calculated by determination of optical density at 475 nanometers and values extrapolated by comparison with a standard curve of determinations for synthetic melanin, a measurement of melanogenesis which correlates extremely well with $^{14}$C-DOPA incorporation and with tyrosinase activity (Friedmann, P. S. and Gilchrest, B. A., *J. Cell. Physiol.* 133:88–94 (1987)). Melanin values were expressed as total melanin per culture, as melanin content per cell, or as percent of untreated controls.

In certain instances, phase contrast micrographs were taken using an inverted microscope after the cultures were washed once with phosphate buffered saline.

EXAMPLE 3

In-Vitro Effect of 1,2-dioctanoylglycerol on Melanin Synthesis in Human Melanocytes Melanocytes of a melanotic cell line issued from a human melanoma obtained as described by J. F. DORE in C. R. Acad. Sci. Paris, band 304, series 111, number 5 (1987) are cultivated in a Dulbecco's Modified Eagle's Medium (DMEM) from GIBCO (France), supplemented with 2.5% of fetal calf serum. These cultures are divided in 5 groups. In the first group, control group, "C" no DAG is added. In the second, third and fourth groups, "G2", "G3" and "G4", 1,2-dioctanoylglycerol (DOG, M.W. 344) is added at the following concentrations: 5 µg/ml (G2), 20 µg/ml (G3) and 30 µg/ml (G4). To the fifth group, "G5", the positive control, 1-oleoyl-2-acetyl-glycerol (OAG, M.W. 398) is added at the concentration of 20 µ/ml. Cultures were initiated at day D, cultures G2 and G4 were treated at day D+1, with DOG and group G5 with OAG by adding these products in the culture medium at these described concentrations.

This treatment was performed again at days D+4 and D+7. At day D+8, the cells were recovered and isolated by centrifugation. The cell pellet was completely dissolved by heating at 60° C. in an amount of 1N KOH solution sufficient to obtain a final solution corresponding to the same concentration of cells for each sample. The Optical Density of the resulting solution was read on a spectrophotometer at the wavelength 405 nanometer appropriate to evaluate the amount of melanin formed by comparison with the optical density obtained with a solution of commercially available synthetic melanin of known concentration (e.g., M8631 from SIGMA France). The cells were also counted, and of the amount of the melanin formed per $10^6$ cells was calculated. The efficiency (E), also referred to herein as activity, of the tested products on the stimulation of melanogenesis was calculated by the following formula:

$$E = \frac{q_p - q_0}{q_0} \times 100$$

wherein q represents the quantity of melanin formed per $10^6$ cells, $q_p$ represents the culture plus DAG to be tested and $q_0$ represents the control culture.

The efficiency (E) of DAG at indicated concentrations, calculated according to the above formula, is set forth in Table I. The tests were performed in triplicate for each concentration of DAG. The values in Table 1 showing the number of cells per dish and the amount of melanin expressed in µg (microgram) per $10^6$ cells are mean values. Statistical evaluation was performed using Student's t test to compare the results between the control cultures and the cultures treated with DAGs.

TABLE I

| Concentration in tested product (µg/ml) | Number of cell +/− standard deviation per dish | Melanin in µg per $10^6$ cells | Efficiency E (%) | Student's t test |
|---|---|---|---|---|
| C: 0 | $(2.54 \pm 0.19) \times 10^6$ | $27.27 \pm 2.01$ | 0 | |
| G2 (DOG): 5 | $(2.50 \pm 0.29) \times 10^6$ | $32.38 \pm 1.76$ | 19 | 0.04 (S*) |
| G3 (DOG): 20 | $(2.42 \pm 0.09) \times 10^6$ | $36.31 \pm 2.65$ | 33 | 0.01 (S*) |
| G4 (DOG): 30 | $(2.34 \pm 0.02) \times 10^6$ | $47.55 \pm 8.02$ | 74 | 0.02 (S*) |
| G5 (OAG): 20 | $(2.25 \pm 0.29) \times 10^6$ | $61.47 \pm 8.71$ | 125 | 0.003 (S*) |

*S = Significant, t ≦5%;
**NS - Not Significant, t >5%

The results shown in Table I demonstrate that DOG significantly enhances, or stimulates the production of melanin. It is important to note that the number of cells per culture remain substantially the same in the treated cultures and in the control cultures, demonstrating that diacylglycerols described in the present invention stimulate melanogenesis at non-cytotoxic doses.

Incorporation of $^{14}$C-DOPA

Melanocytes cultures as described above were initiated and again subdivided into five groups, C, G2, G3, G4 and G5, and DAGs added as described above. However, at the day D+8, $^{14}$C-DOPA (L-DOPA (L-3,4-dihydroxyphenyl alanine) constitutes a precursor in the well known melanin synthesis chain) was added to all cultures, including the control. The cultures were then incubated under standard conditions for 72 hours.

At day D+11, the amount of $^{14}$C-DOPA incorporated in the melanocytes was evaluated. After counting the cells, the cells were treated with 5% trichloracetic acid to precipitate cellular proteins. The precipitated proteins were retained on a fiberglass filter and rinsed with ethanol. The radioactivity of the precipitated cells, which is directly proportional to the incorporation of $^{14}$C-DOPA in the melanocytes, was measured by liquid scintillation methods well known to one skilled in the art.

The efficiency (E) of the tested DAGs on the incorporation of $^{14}$C-DOPA was calculated according to the formula described above. The results are set forth in Table II:

TABLE II

| Concentration in tested product (µg/ml) | Number of cell +/− standard deviation per dish | Radioactivity (cpm per $10^6$ cells) | Efficiency E (%) | Student's t test |
|---|---|---|---|---|
| T: 0 | $(0.668 \pm 0.028) \times 10^6$ | 846 ± 15 | 0 | |
| G2 (DOG): 5 | $(0.668 \pm 0.057) \times 10^6$ | 1041 ± 75 | 23 | 0.04 (S*) |
| G3 (DOG): 20 | $(0.731 \pm 0.036) \times 10^6$ | 1164 ± 247 | 38 | NS* |
| G4 (DOG): 30 | $(0.714 \pm 0.080) \times 10^6$ | 1507 ± 225 | 78 | 0.03 (S*) |
| G59 (OAG): 20 | $(0.314 \pm 0.090) \times 10^6$ | 1403 ± 103 | 66 | 0.006 (S*) |

*S = Significant t ≦5%;
**NS - Non Significant*, t >5%

The results shown in Table II clearly demonstrate that diacylglycerols described in the present invention, tested under the circumstances described above, significantly increase the incorporation of $^{14}$C-DOPA in the melanocytes and thus, evidences the positive activity of DAGs in melanogenesis in human melanocytes.

EXAMPLE 4

In-Vivo Experiments with Adult Guinea Pigs

Preparations: 1-oleoyl-2-acetyl-sn-glycerol (OAG), 1,2 dioctanoyl-sn-glycerol (diC$_8$), and 1,2 dipalmitoyl-sn-glycerol (diC$_{16}$) supplied in chloroform (Avanti; Polar Lipids, Inc., Alabanter, Ala.) were dried under continuous-steam nitrogen gas and immediately dissolved in propylene glycol (Sigma, St. Louis, Mo.) to the desired concentrations. 1 oleoyl-2-acetyl-rac-glycerol (racemic) in pure form (Sigma, St. Louis, Mo.) was dissolved in propylene glycol directly. The preparations were divided into daily application doses, sealed in microfuge tubes, purged with nitrogen and stored at −20° C. until used. As a vehicle control, propylene glycol (Sigma) was divided into daily application doses, sealed, and stored identically to the diacylglycerol preparations. The diacylglycerol were applied in 20 µl volumes, sufficient to cover the test site.

Animals: Outbred pigmented guinea pigs, American Shorthair X Abyssinian (Kulper Rabbit Ranch, Chicago, Ill.), ranged in age from 10 to 16 weeks at the beginning of the study. The animals had free access to guinea pig chow and chlorinated water and were housed in individual cages. Prior to topical applications, each animal was shaved with an electric razor (Oster, #40 blade) to remove the long hair. The remaining stubble was removed with the commercially available depilatory, Nair (Carter-Wallace). Application test sites of one square centimeter were chosen in areas of comparable baseline pigmentation and were delineated with an indelible marker in order to relocate the sites for subsequent daily applications.

U. V. Irradiation: The radiation source consisted of two Sylvania FS40UVB bulbs. The irradiance, measured through a quartz filter by a K700A research photometer (International Light, Newburyport, Mass.) fitted with a UVB probe (detector SSE 240, diffuser W, filter UVB, 290±5 nm) was $2.6 \times 10^{-4}$ w/cm$^2$. The animals were restrained by hand and exposed through an adhesive template daily during two work weeks (10 days) for 3 min. 12 sec. (70 mJ/cm$_2$), a 0.6 MED dose in representative animals. Guinea pigs thus received a total of 700 mJ/CM$^2$ over the 10 day period.

Experimental Protocol: Four separate treatment groups each contained 4–6 guinea pigs. Group 1 animals were treated with vehicle alone and four separate concentrations of OAG (20, 30, 40 and 60 mg/ml) once daily for five days. Group 2 animals were treated with Vehicle along and five separate concentrations of OAG (10, 20, 30, 40 and 60 mg/ml) either once or twice daily for five days. Group 3 animals received twice daily applications for five days of 50 mg/ml OAG(sn), OAG(rac), diC$_8$, and diC$_{16}$ as well as vehicle alone. Group 4 animals received OAG (25 mg/ml) 3 times daily to one site and the estimated 0.6 MED dose to a second site daily for 10 days.

Evaluation of Pigmentation: The test sites were examined weekly and graded using the following visual scale: 0-no change from baseline color; ± hyperpigmentation present, but indistinct; +1- slight darkening, easily discernable; +2-moderate, even darkening; +3-substantial even darkening; and +4-profound, even darkening. Photographs were taken to document observations. Prior to each weekly observation, the animals were re-shaved to remove the rapidly growing hair. From representative animals, biopsies were taken for histologic analysis.

Histologic Analysis: Punch biopsies (4 mm) were taken from normal skin, vehicle-treated skin and pigmented test sites on Day 19 to 25. Specimens were fixed in formation (10%) and vertical cross sections, stained with both Hematoxylin and Eosin (H&E) and Fontana-Messon stains were examined under 10× and 40× magnification using an Olympus microscope. The amount of epidermis occupied by melanin was quantitated by computer image analysis previously described (Bhawan, J. et al., Arch. Dermalol., 127:666–672 (1991)).

RESULTS

Figure 7:
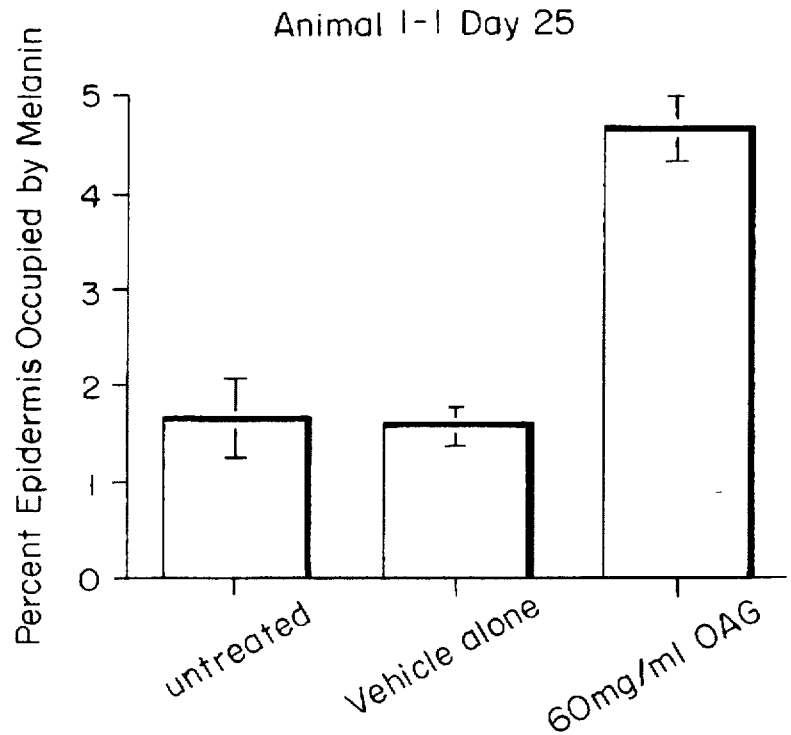
FIG. 7 is a graphic representation depicting the percent epidermis occupied by melanin in control animals and diacylglycerol-treated animals (1-site treatment).
Figure 8:
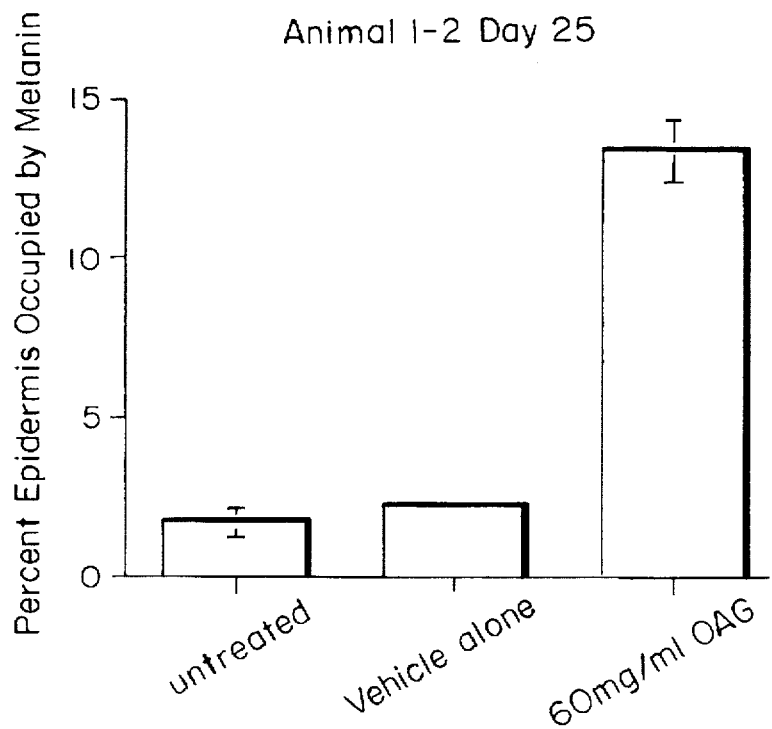
FIG. 8 is a graphic representation depicting the percent epidermis occupied by melanin in control animals and diacylglycerol-treated animals (2-site treatment).
Figure 9:
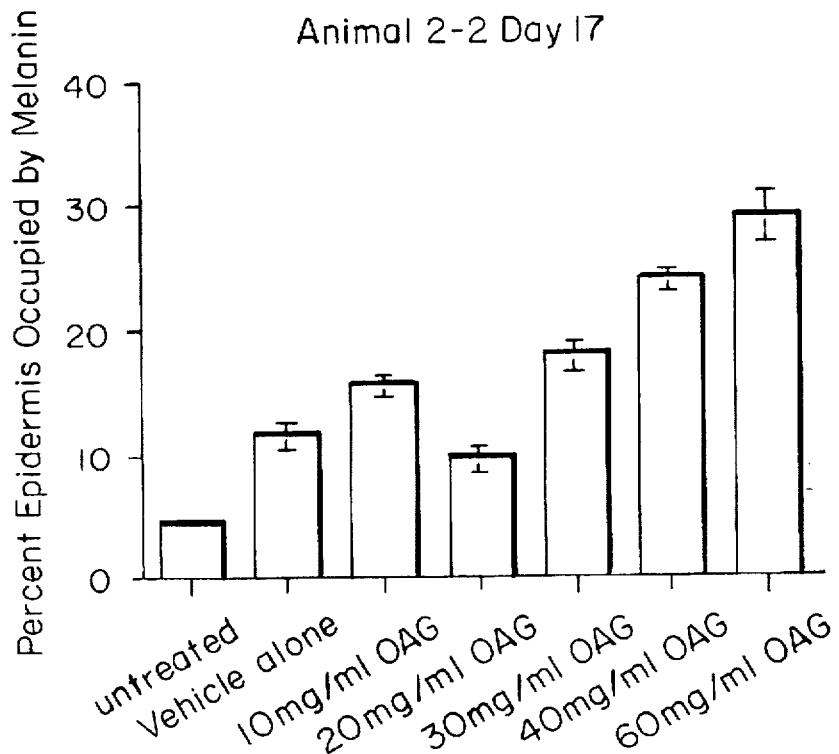
FIG. 9 is a graphic representation depicting the percent epidermis occupied by melanin in control animals and animals treated with various concentrations of the diacylglycerol, 1-oleoly-2-acetyl-glycerol.

OAG Concentrations: Erythema and scale were noted in most OAG test sites during the application week. Dose-dependent OAG-induced pigmentation was first seen in three of four animals in group 1 within 17 days after the last of 5 daily applications (Table III). The pigmentation showed a broad peak of maximal intensity between days 17 and 33 and persisted for at least 60 days in all animals, being last observed on day 60 to day 73. Enhanced pigmentation was not seen in vehicle treated test sites. Computerized image analysis of melanin content performed on biopsies taken from normal and vehicle-treated skin and from the 60 mg/ml OAG site revealed an increase in melanin content in the OAG-treated site (FIG. 7). Group 2 animals received the same OAG concentration as group 1, but with one additional site receiving a lower OAG concentration of 10 mg/ml. The epidermal melanin content, as analyzed by computer image analysis, tended to increase as the concentration increased (FIG. 8). A representative animal receiving twice daily applications is shown in FIG. 9.

TABLE III

| | ANIMALS | | |
|---|---|---|---|
| | 1-1 | 1-2 | 1-3 |
| Propylene Glycol | 0 | 0 | 0 |
| OAG (sn) 20 mg/ml | 1 | 1 | 1 |
| OAG (sn) 30 mg/ml | 1 | 2 | 1 |
| OAG (sn) 40 mg/ml | 2 | 3 | 1 |
| OAG (sn) 60 mg/ml | 3 | 3 | 2 |

Maximum Hperpigmentation (0–4 scale)

Figure 10:
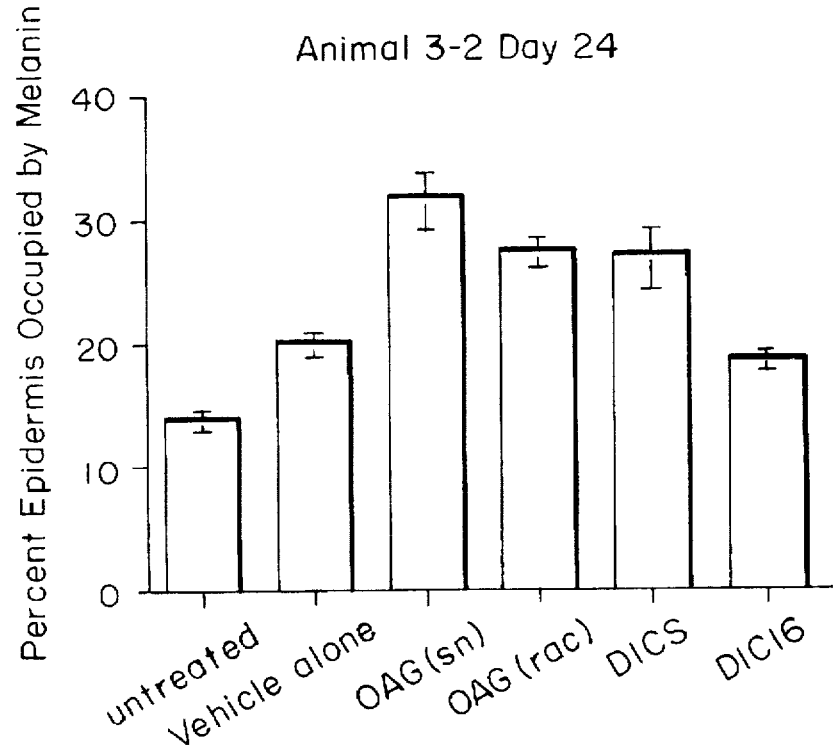
FIG. 10 is a graphic representation depicting the percent epidermis occupied by melanin in control animals and animals treated with four diacylglycerols, 1-oleoly-2-acetylglycerol (sn); 1-oleoly-2-acetyl-glycerol (rac); dioctanoylglycerol (diC$_8$) and dipalmitoylglycerol (diC$_{16}$).

Efficacy of OAG Analogues: Increased peak pigmentation +1 to +2 was seen in five of five animals in the OAG(sn), OAG(rac) sites and diC$_8$ sites (FIG. 10 and Table IV). No reaction was seen in the vehicle or diC$_{16}$ sites. The enhanced pigmentation was comparable for the three DAGs and persisted over three months (104–148 days).

TABLE IV

| | ANIMALS | | | | |
|---|---|---|---|---|---|
| | 3-1 | 3-2 | 3-3 | 3-4 | 3-5 |
| Propylene Glycol | 0 | 0 | 0 | 0 | 0 |
| OAG (sn) 50 mg/ml | 2 | 2 | 1 | 1 | 1 |
| OAG (rac) 50 mg/ml | 1 | 2 | 2 | 1 | 1 |
| DIC$_8$ 50 mg/ml | 1 | 2 | 1 | 2 | 2 |
| DIC$_{16}$ 50 mg/ml | 0 | 0 | 0 | 0 | 0 |

Maximum Hyperpigmentation (0–4 scale)

Figure 11:
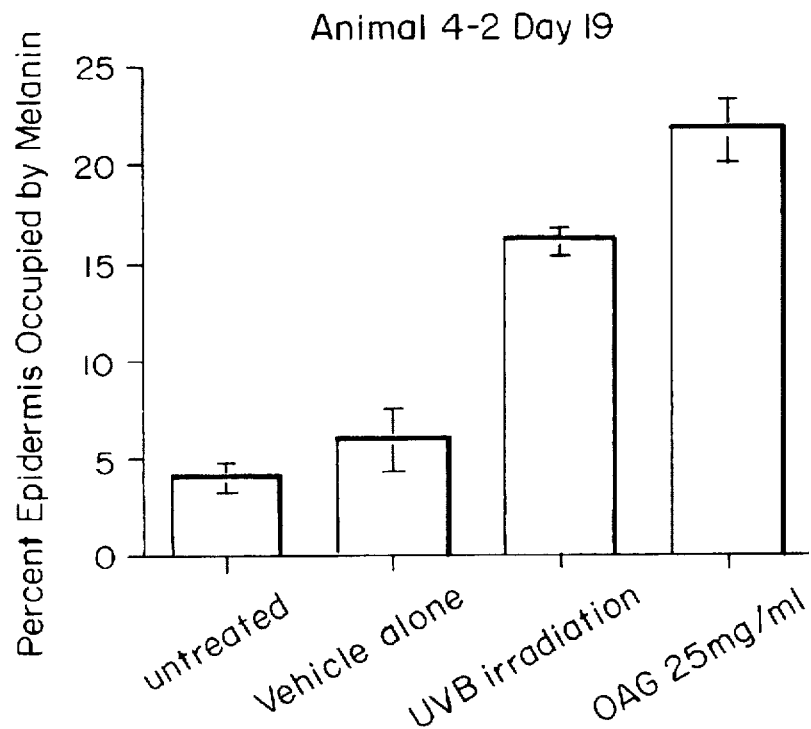
FIG. 11 is a graphic representation depicting the percent epidermis occupied by melanin in control animals, animals exposed to UVB radiation and diacylglycerol-treated animals.
Figure 12:
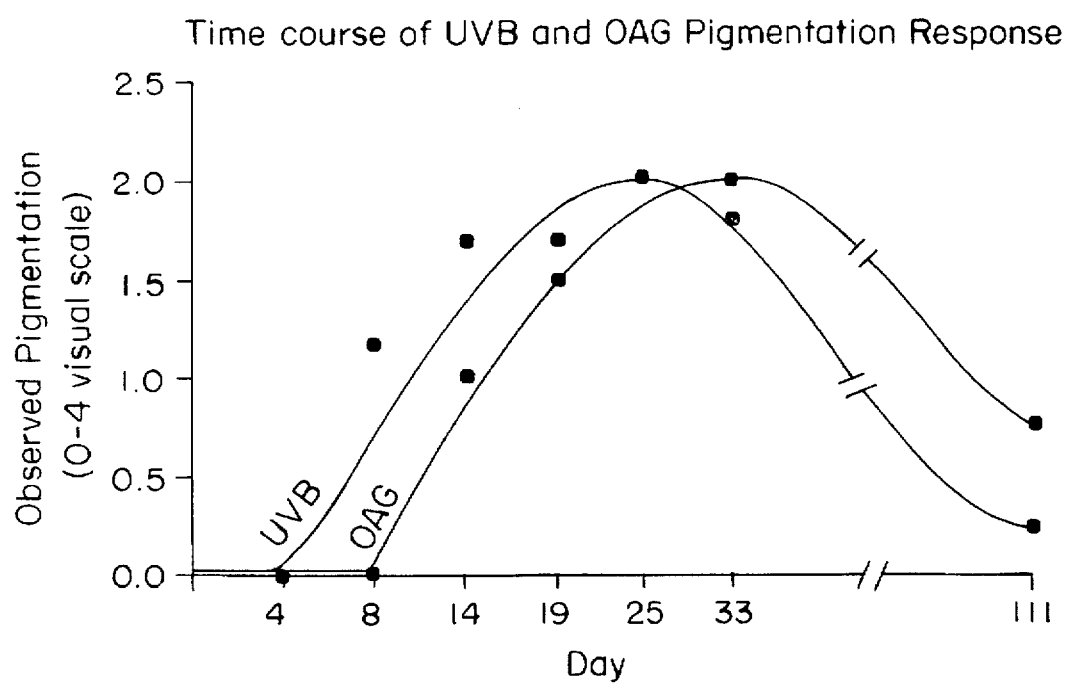
FIG. 12 is a graphic representation depicting observed pigmentation over a course of time for control animals and animals treated with a diacylglycerol, 1-oleoly-2-acetylglycerol.

OAG versus UV Irradiation: In all 6 animals the OAG 25 mg/ml test sites and UVB sites developed a +2 to +3 enhanced even pigmentation (FIG. 11 and Table V, observed on day 22). The time course for the OAG-induced and UV-induced responses were comparable with pigmentation appearing on average 4 days later in OAG test sites (FIG. 12). Clinically, the increased pigmentation induced by OAG was indistinguishable from that stimulated by UVB. Computer image analysis of the melanin content revealed that OAG 25 mg/ml, 3 times daily, stimulated pigmentation to a grater degree than 70 mJ/cm$^2$ each day for 10 days (FIG. 7).

TABLE V

| | ANIMALS | | | | | |
|---|---|---|---|---|---|---|
| | 4-1 | 4-2 | 4-3 | 4-4 | 4-5 | 4-6 |
| Propylene Glycol | 0 | 0 | 0 | 0 | 0 | 0 |
| OAG (sn) 50 mg/ml | 2 | 2 | 3 | 2 | 2 | 3 |
| UVB | 2 | 2 | 2 | 2 | 2 | 3 |

Maximum Hyperpigmentation (0–4 scale)

Figure 5:
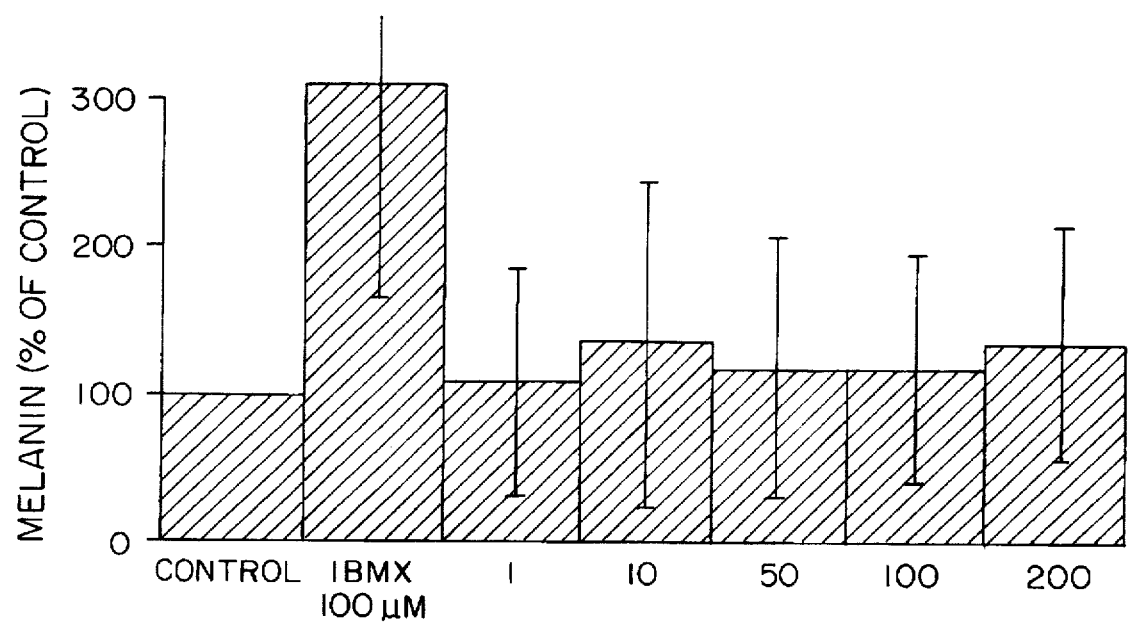
FIG. 5 is a graph illustrating the effects of a diacylglycerol, 1-oleoyl-2-acetyl-glycerol, upon the melanin content of S91 murine melanoma cells in culture.

Histology: H&E stained sections of DAG-treated skin 19 to 25 days after the last application were similar to vehicle-treated or untreated sections except for mild acanthosis, as previously reported in DAG-treated skin (Smart, R. C., et al., "Comparison of The Effect of sh 1,2-didecanoylglycerol and 12-O-tetradecanoyl-phorbol-13-acetate on Cutaneous Morphology, Inflammation and Tumor Promotion in CD-1 Mice", *Cardinogenesis*, 9:2221–2226, (1988)). In no case were the dermal melanophages present. Examination of untreated guinea pig skin stained with Fontana-Masson stain to identify melanin in randomly oriented sections revealed an irregular distribution of melanocytes in the epidermal basal layer with some sparing of follicular ostia. Macroscopically, on close inspection of the guinea pig skin after gentle stretching, linear striations of pigmentation were visible (FIG. 5). Analysis of this pigmentation pattern in the biopsy sections suggested that the pigmented striations represented melanin contained in the interfollicular epidermis and the lighter bands corresponded to follicular ostia. Developmentally hair follicles are known to be distributed linearly, therefore, precise orientation of the embedded skin biopsies with respect to the hair follicles was important for quantitative histologic analysis. Computer image analysis of epidermal melanin content in all specimens was based on the average total area of epidermis covered by melanin in 4–6 histologic sections.

Topical application of OAG increased melanin content compared to untreated skin, but did not appear to alter the irregular distribution of melanocytes. The most prominent increase occurred in the basal layers but keratinocytes throughout the epidermis of OAG-treated skin contained more melanin than in control skin, often with a pattern of nuclear 'capping'. A similar increase in melanin content was seen in the analogous diC$_8$ sites, but not diC$_{16}$ sites, corresponding to the clinical appearance of the skin. The pattern of increased epidermal melanin content in DAG-treated skin was indistinguishable from that induced by UVB (FIG. 8).

EXAMPLE 5

DAG Composition as an Emulsion

Two different phases were combined to form the preparation:

| Phase A | |
|---|---|
| 1-oleoyl-2-acetyl-glycerol | 0.5 g |
| Miglyol 812 ® (a triglyceride oily mixture in C8–C12, C.A.S. Reg. number 123465-33-8) | 10 g |
| Phase B: | |
| Excipient for emulsion (including 10% of Miglyol 812 ® and 2% of Carbopol 1342 ®) | qsp to 100 g with phase A |

Moderate heating at 30° C. was preferred for preparing Phase A. Phase A was emulsified to Phase B by standard emulsifying processes well known to those skilled in the art. The resulting emulsion, when applied to the skin or scalp, will stimulate tanning of skin or darkening of hair even without specific exposure to ultraviolet radiation.

EXAMPLE 6

DAG Composition as a Micro Emulsion

This composition comprises the following components:

| | |
|---|---|
| 1,2-dioctanoylglycerol | 5% |
| Brij96 ® (a polyethyleneglycol mono-9-octadecenyl ether) | 5% |
| dipropyleneglycol | 45% |
| Water | qsp 100% |

The micro emulsion is prepared by admixing all components at room temperature until a slightly viscous, homogeneous, transparent liquid is obtained. The admixture is prepared in a glass vessel containing a magnetic bar and stirred vigorously over a period of about 30 minutes. The micro emulsion obtained is remarkably stable. This DAG micro emulsion may be applied to the skin or scalp and will stimulate tanning of skin and darkening of hair even without specific exposure to ultraviolet radiation.

17

EXAMPLE 7

DAG Composition as a Micro Emulsion

This composition comprises the following components:

| | |
|---|---|
| 1,2-didecanoylglycerol | 2% |
| Miglycol 812® | 15% |
| Brij96® | 10% |
| Dipropyleneglycol | 36.5% |
| Water | qsp 100% |

The micro emulsion is prepared as described in Example 6. This DAG micro emulsion may be applied to the skin or scalp and will stimulate tanning of skin and darkening of hair even without specific exposure to ultraviolet radiation.

EXAMPLE 8

DAG Composition as a Micro Emulsion

This composition comprises the following components:

| | |
|---|---|
| 1,2-didecanoylglycerol | 5% |
| Miglycol 812® | 15% |
| Brij96® | 10% |
| Dipropyleneglycol | 35% |
| Water | qsp 100% |

The micro emulsion is prepared as described in Example 6. This DAG micro emulsion may be applied to the skin or scalp and will stimulate tanning of skin and darkening of hair even without specific exposure ultraviolet radiation.

EXAMPLE 9

Hydro Alcoholic Lotion Containing OAG

The hydro alcoholic composition comprises the following components:

| | |
|---|---|
| 1-oleoyl-2-acetyl-glycerol (OAG) | 1% |
| Perfumed hydro alcoholic excipient at 5% in ethanol | qsp 100% |

The OAG is admixed with the perfumed hydro alcoholic excipient at 50% ethanol pentyl solution. This lotion may be applied to the scalp to provide a darkening of hair, or to delay graying of hair.

In the full description and claims all the percentages are give by weight unless otherwise stated.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of increasing pigmentation of vertebrate skin by increasing the melanin content of melanocytes present in vertebrate skin comprising topically applying to the skin of the vertebrate, or subcutaneously administering to the vertebrate, an effective amount of a diacylglycerol wherein the diacylglycerol comprises a hydroxyl in the three position and two carboxylic acid esters in the one and two positions, said carboxylic acid esters having from one to twenty four carbon atoms, and which enhances melanin synthesis in the melanocytes.

2. The method of claim 1, wherein the diacylglycerol is 1-oleoyl-2-acetyl-glycerol.

3. The method of claim 1, wherein the diacylglycerol is 1,2-dioctanoylglycerol.

4. The method of claim 1, wherein the diacylglycerol is 1,2-didecanoylglycerol.

5. The method of claim 1, wherein the vertebrate is a human being.

6. The method of claim 1, wherein the pigmentation of skin occurs irrespective of exposure to an irradiation selected from the group consisting of ultraviolet irradiation and sunlight irradiation.

7. The method of claim 1, wherein the effective amount of the diacylglycerol is present in a composition containing from 0.1 to 10% by weight of diacylglycerol with respect to the total weight of the composition.

8. The method of claim 7 further comprising admixing the diacylglycerol with a topically acceptable carrier selected from the group consisting of water, glycerol, alcohol, propyleneglycol, a fatty alcohol, a triglyceride a fatty acid ester, a mineral oil, liquid petrolatum, isopropyl palmitate, polyethylene glycol, ethanol, polyoxyethylene monolaurate at 5% in water, sodium lauryl sulfate at 5% in water and mixtures thereof.

9. A method of increasing pigmentation of acquired or congenital white patches of skin of a vertebrate comprising the implantation of skin grafts on the patches, the skin grafts comprising melanocytes activated by contact with an effective amount of a diacylglycerol which wherein the diacylglycerol comprises a hydroxyl in the three position and two carboxylic acid esters in the one and two positions, said carboxylic acid esters having from one to twenty-four carbon atoms, and enhances melanin synthesis in the melanocytes.

10. The method of claim 9, wherein the patches of skin to be pigmented are vitiligo patches.

11. The method of claim 9, wherein the diacylglycerol is 1-oleoyl-2-acetyl-glycerol.

12. The method of claim 9, wherein the diacylglycerol is 1,2-dioctanoylglycerol.

13. The method of claim 9, wherein the diacylglyercol is 1,2-didecanoylglycerol.

14. The method of claim 9, wherein the vertebrate is a human being.

15. The method of claim 9, wherein the pigmentation occurs irrespective of exposure to an irradiation selected from the group consisting of ultraviolet irradiation and sunlight irradiation.

16. The method of claim 9, wherein the effective amount of the diacylglycerol ranges from 10 µM to 1000 µM.

17. The method of claim 16 wherein the effective amount of the diacylglycerol ranges from 50 µM to 300 µM.

* * * * *